US009151438B2

(12) United States Patent
Shirkhodaie et al.

(10) Patent No.: US 9,151,438 B2
(45) Date of Patent: Oct. 6, 2015

(54) AUTOMATED OBJECT MANIPULATION SYSTEM

(75) Inventors: Amir Shirkhodaie, Nashville, TN (US); Robert Moriarty, Greewood, IN (US); Kong Ma, Carmel, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 658 days.

(21) Appl. No.: 13/416,705

(22) Filed: Mar. 9, 2012

(65) Prior Publication Data
US 2012/0230807 A1 Sep. 13, 2012

Related U.S. Application Data

(60) Provisional application No. 61/450,973, filed on Mar. 9, 2011.

(51) Int. Cl.
*B65G 47/90* (2006.01)
*F16M 11/12* (2006.01)
*F16M 11/18* (2006.01)
*G01N 21/95* (2006.01)

(52) U.S. Cl.
CPC ............ *F16M 11/123* (2013.01); *F16M 11/18* (2013.01); *B65G 47/904* (2013.01); *G01N 21/95* (2013.01)

(58) Field of Classification Search
CPC ........ B25J 13/08; B25J 15/02; B25J 15/0253; B25J 15/08; B25J 15/10; B25J 17/02; B60P 1/02; B60P 1/022; B60P 1/025; B60P 1/027; B62B 3/0606; B62B 3/0612; B62B 3/0618; B62B 3/0625; B62B 3/0631; F16M 11/123; F16M 11/18; G01N 21/95
USPC ............... 294/119.1; 414/1, 4, 736, 763, 774, 414/783, 815, 816; 901/23, 29, 31, 32, 46
See application file for complete search history.

(56) References Cited

U.S. PATENT DOCUMENTS

| | | | |
|---|---|---|---|
| 2,695,715 A | 11/1954 | Goertz et al. | |
| 3,874,525 A | 4/1975 | Hassan et al. | |
| 4,229,641 A | 10/1980 | Ihara | |
| 4,607,873 A | 8/1986 | Nusbaumer et al. | |
| 4,626,013 A | 12/1986 | Barrows | |
| 4,865,514 A * | 9/1989 | Tsuchihashi et al. | 414/736 |
| 5,528,955 A * | 6/1996 | Hannaford et al. | 74/490.01 |
| 5,811,951 A * | 9/1998 | Young | 318/568.2 |
| 2001/0047589 A1 | 12/2001 | Conte | |
| 2008/0181759 A1 | 7/2008 | Gaegauf et al. | |
| 2008/0278105 A1 | 11/2008 | Somes | |

OTHER PUBLICATIONS

International Search Report and Written Opinion, ISA/US, PCT/US2012/028523, Rolls-Royce Corporation, May 25, 2012.

* cited by examiner

*Primary Examiner* — Saul Rodriguez
*Assistant Examiner* — Brendan Tighe
(74) *Attorney, Agent, or Firm* — Shumaker & Sieffert, P.A.

(57) ABSTRACT

An apparatus of an automated object manipulation system includes a support base; a finger assembly mechanically coupled to the support base; a first drive unit operable to rotate the finger assembly about a first axis; a second drive unit operable to rotate the finger assembly about a second axis; a third drive unit operable to rotate the finger assembly about a third axis, and a processor capable of conducting a profile assessment; determining a manipulation program in response to the profile assessment; and controlling the finger assembly in response to the manipulation program where the finger assembly has a support bracket with a set of parallel jaws and the support bracket is mechanically coupled to the first drive unit, a linking bracket mechanically coupled to the second drive unit and a circular frame mechanically coupled to the finger assembly and the third drive unit.

7 Claims, 8 Drawing Sheets

AUTOMATED OBJECT MANIPULATION SYSTEM

CROSS REFERENCE TO RELATED APPLICATIONS

The present application claims the benefit of U.S. Provisional Patent Application 61/450,973, filed Mar. 9, 2011, and is incorporated herein by reference. This application also incorporates by reference, in their entirety, the following concurrently filed applications: INTELLIGENT AIRFOIL COMPONENT SURFACE IMAGING INSPECTION, Ser. No. 13/416,315, issued as U.S. Pat. No. 8,768,041 on Jul. 1, 2014; INTELLIGENT AIRFOIL COMPONENT GRAIN DEFECT INSPECTION, Ser. No. 13/416,516; INTELLIGENT AIRFOIL COMPONENT SURFACE INSPECTION, Ser. No. 13/416,409; PROTOCOL-BASED INSPECTION SYSTEM, Ser. No. 13/416,610, and ILLUMINATION SYSTEM WITH ILLUMINATION SHIELD, Ser. No. 13/416,770, issued as U.S. Pat. No. 8,346,924 on Jun. 10, 2014.

TECHNICAL FIELD

The present invention generally relates to automated object manipulation systems, and more particularly, but not exclusively, to automated object analysis manipulators.

BACKGROUND

Present approaches to object manipulation suffer from a variety of drawbacks, limitations, disadvantages and problems including those respecting efficiency, repeatability and others. There is a need for the unique and inventive automated object analysis manipulator apparatuses, systems and methods disclosed herein.

SUMMARY

One embodiment of the present invention is a unique automated object manipulation system. Other embodiments include apparatuses, systems, devices, hardware, methods, and combinations for an automated object manipulation system. Further embodiments, forms, features, aspects, benefits, and advantages of the present application shall become apparent from the description and figures provided herewith.

DETAILED DESCRIPTION OF THE ILLUSTRATIVE EMBODIMENTS

Figure 1:
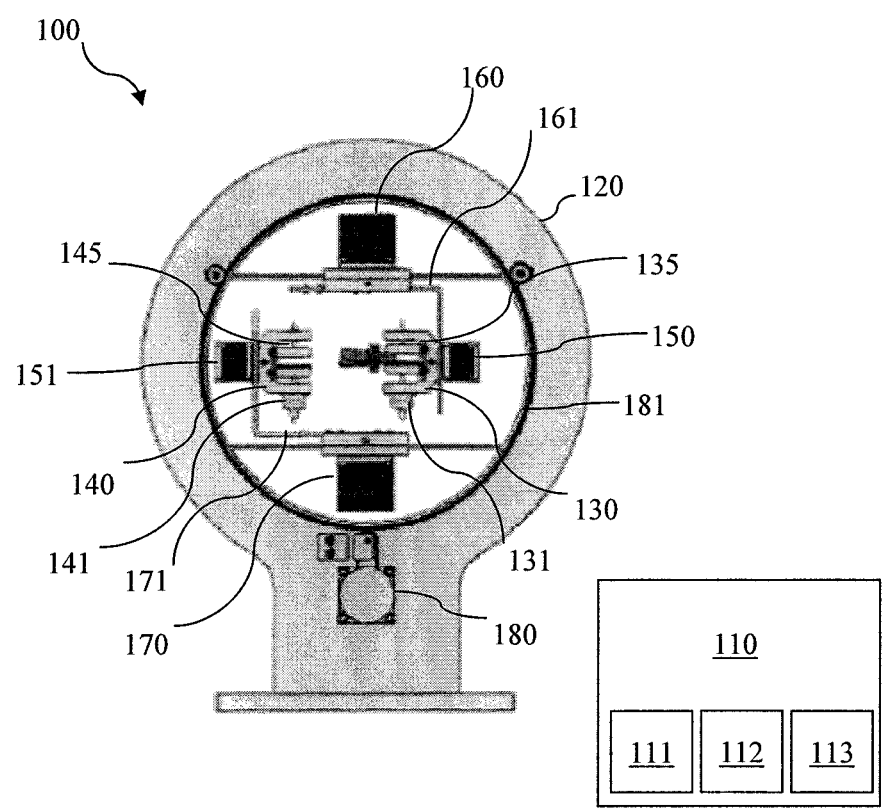
FIG. 1 is an illustration of an embodiment of an object manipulation system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With reference to FIG. 1, one embodiment of an automated object manipulation system 100 includes a support structure 120 and two robotic fingers 130, 140 each with five degrees of freedom, but other embodiments of the system 100 can include greater or fewer freedoms. The five degrees of freedom can include, but are not limited to, three degrees of rotational freedom and two degrees of linear freedom. In one embodiment, the degrees of rotational freedom provide object positioning capabilities during an object analysis process while the two degrees of linear freedom aid in object capture and alignment. In one embodiment, an automated object manipulation system can include a single robotic finger. Robotic fingers or end effectors capable of physically grasping an object with direct force can include various forms of mechanical grippers including parallel jaws, claws, grapples, tongs, multiple fingers, and the like.

In FIG. 1, robotic fingers 130, 140 are shown to have a sliding drive 131, 141 for opening and closing a set of parallel jaws 135, 145. Robotic fingers 130, 140 are further shown having a y-axis rotary drive 150, 151 which is capable of providing a degree of rotational freedom about the y-axis. An L-bracket 161, 171 is shown linking robotic fingers 130, 140 with a z-axis rotary drive 160, 170. Z-axis rotary drives 160, 170 are capable of providing a degree of rotational freedom about the z-axis. Robotic fingers 130, 140 share a circular frame 181 with an orientation controlled by an x-axis rotary drive 180 shown mounted below circular frame 181. X-axis rotary drive 180 is capable of providing a degree of rotational freedom about the x-axis. Circular frame 181 is shown housed inside a cavity of support structure 120. For exemplary purposes, embodiments are described with a right-hand coordinate frame and should not be construed as limiting.

In one embodiment of FIG. 1, object manipulation system 100 is controlled by a processor 110. Processor 110 can contain modules for predetermined object manipulation by the fingers and thereby the fingers are capable of positioning the object in various positions to provide automated object presentation during an analysis. Processor 110 is represented as a single component containing hardware capable of performing various functions. Each function can be located on a separate piece of hardware and can be one of several hardware varieties available and arranged by one skilled in the art. Processor 110 can also include one or more microprocessors where in one embodiment a single microprocessor can provide the function of each module or separate microprocessors can be used for one or more of the modules.

In a further embodiment, processor 110 can include a data storage module 111, an instruction module 112 and a control module 113. Computerized control can allow preprogrammed and operator initiated control of object manipulation system 100. Control module 113 can provide object features and position data from a sensor resulting from an object assessment. The feature and position data can be fed to instruction module 112. Instruction module 112 can supply preprogrammed manipulation instructions in response to the feature and position data of the object assessment. The preprogrammed manipulation instructions can be retrieved from data storage module 111. In a further embodiment, the feature and position data from the object assessment can be stored in data storage module 111.

In another embodiment, a processor can include manipulation instructions which are capable of controlling the position and alignment of an object in relation to a sensor for an object analysis in response to data obtained by a profiling assessment. A profiling assessment of an object can provide identification features to be used to establish a profile and preprogrammed manipulation during the object analysis. A mark or feature can be used to establish a zero reference point. An automated object manipulation system can allow for repeatable analysis on multiple objects utilizing object features and preprogrammed manipulation.

In yet another embodiment, a processor can include programming to continuously interpret data received from profiling assessments and object analysis in a repeatable manner, for instance. Object manipulation by finger assemblies of a manipulation system in response to an analysis program from a processor can repeatedly provide data including the positions of an object and indications of features above and below the surface as well as anomalies. For a further embodiment, once a first finger assembly has completed an assigned task, the object can be transferred to a second finger assembly in order to continue inspection of another end of the object.

One embodiment of the present application can include multiple stepper motors, position encoders, and limit switches to name a few which can be used to controllably position objects with the finger assemblies of a manipulation system. In a specific embodiment, a drive motor and position encoder can be included for each degree of freedom, which in some cases can be five degrees, to allow exposure of the object surfaces to a sensor. In another embodiment, a processor can receive input signals from transducers and position encoders associated with each degree of freedom where the signals can be incorporated as part of the object manipulation programming.

Figure 2:
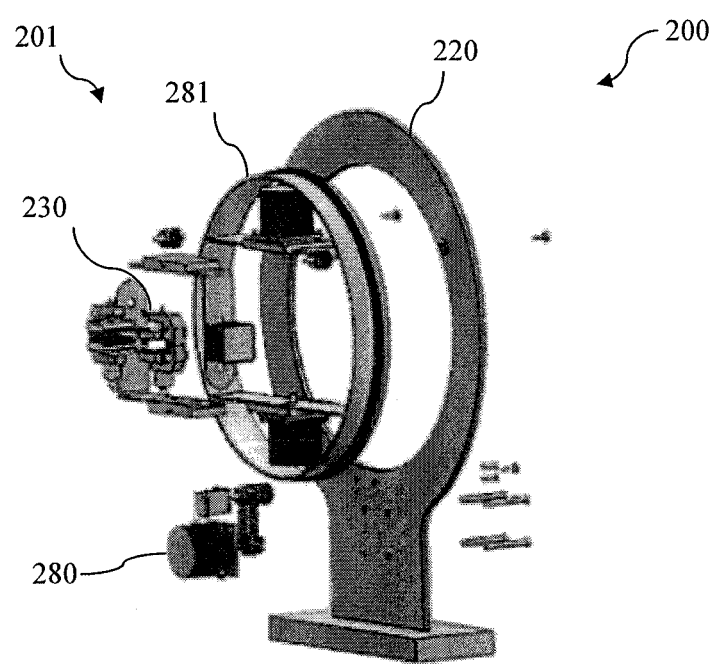
FIG. 2 is an exploded view of an embodiment of an object manipulation system.

FIG. 2 illustrates an exploded view of a manipulation system 200 of one embodiment of the present application. In a specific embodiment, a finger assembly 230 can be installed on a circular frame 281 mechanically coupling finger assembly 230 and a rotary drive 280 and then the entire circular frame assembly 201 can be mounted inside the cavity of a support structure 220. In other embodiments, the circular frame can be integrally manufactured in the support structure and the finger assembly can be installed on to the circular frame as part of the support structure. Assembly parameters and procedures can be determined based on the size and profile of the objects being analyzed as would be known to one skilled in the art.

Figure 3C:
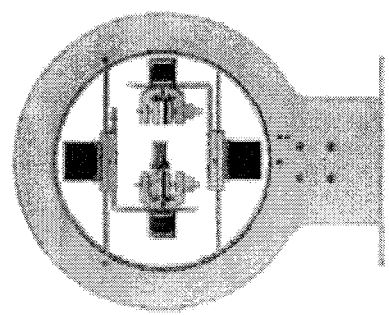
FIG. 3c is a back view illustration of an embodiment of an object manipulation system.
Figure 3B:
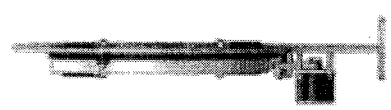
FIG. 3b is a side view illustration of an embodiment of an object manipulation system.
Figure 3A:
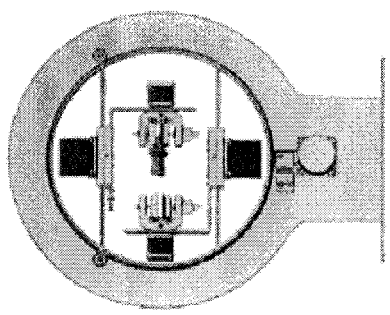
FIG. 3a is a front view illustration of an embodiment of an object manipulation system.

FIGS. 3a, 3b, and 3c illustrate three views of one embodiment of an automated object manipulation system 300. FIG. 3a is representative of a front view. FIG. 3b is representative of a side view. FIG. 3c is representative of a back view. System 300 can be adjusted to accommodate objects of varying sizes and profiles.

Figure 4A:
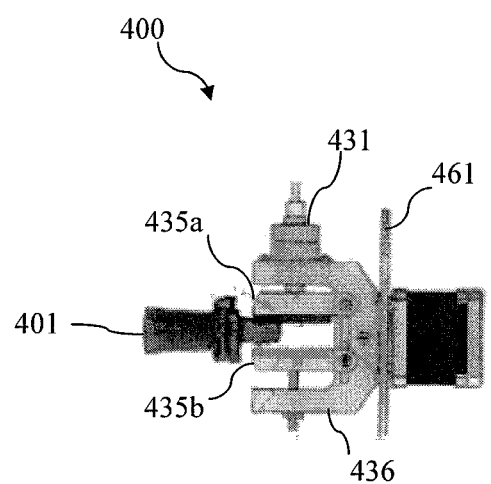
FIGS. 4a and 4b are illustrations of an embodiment of an object manipulation system.
Figure 4B:
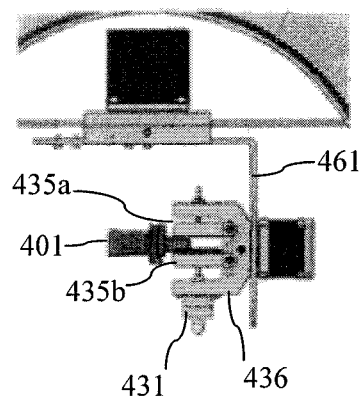

FIGS. 4a and 4b illustrate one embodiment of a finger assembly 400 showing a C-bracket 436 with an L-bracket linking structure 461 and an alignment system 431 including adjustable parallel jaws 435a, 435b for holding an object 401 securely. Parallel jaws 435a, 435b are operated up and down by drive system 431 to accommodate varying sizes and shapes of objects 401. The L-bracket linking structure 461 can be slidingly received with a component that allows the finger assembly 400 to be adjusted toward or away from the opposing finger assembly (not shown). In this way the finger assemblies can be adjusted to alter the gap between the assemblies. The bracket between the rotary drive and the finger assembly is one example of a device that permits the L-bracket linking structure 461 to be adjusted. In one embodiment the jaw 435a can be slidingly adjusted relative to the C-bracket 436 using a screw depicted at the top of the C-bracket, while the jaw 435b is adjusted relative to the C-bracket using the drive system 431. In this way the jaw 435a is relatively static and the jaw 435b is usually moveable to capture or release the object 401. Other manners of driving the jaws 435a and 435b are contemplated herein.

Figure 5:
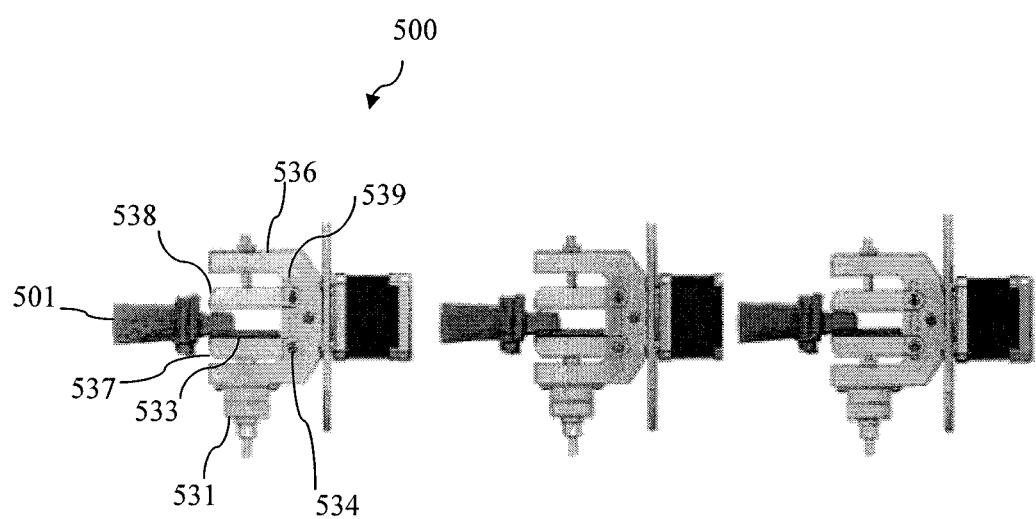
FIG. 5 is an illustration of a portion of an embodiment of an object manipulation system.

FIG. 5 illustrates movement in one embodiment of the parallel jaws on a finger assembly. Finger assembly 500 shown here includes a support bracket 536 and two parallel jaws—a first jaw 537 and a second jaw 538. Second jaw 538 height can be adjustable by a drive system 531, a screw or other such means to accommodate objects 501 with different dimensions. First jaw 537 displacement can be controlled by a small scale linear actuator 534. In other embodiments, the mechanism of drive system 531 and actuator 534 can be alternated or the displacement adjustment can be controlled or accomplished using other mechanisms known in the art. To allow repeatability of the grip of parallel jaws 537, 538, jaws 537, 538 slide up and down a grooved slot 539 on support bracket 536 housing parallel jaws 537, 538. This arrangement can allow a secure alignment of parallel jaws 537, 538 with respect to object 501 and improve analysis repeatability.

The position of first jaw 657 and second jaw 538 are adjusted to an open position allowing placement of an object 501 between jaws 537, 538. Jaws 537, 538 are then adjusted to a closed position thereby holding object 501 for manipulation and analysis. Parallel jaws 537, 538 of finger assembly 500 can include pads 533 which can be replaceable and/or constructed of a high density polymer material to facilitate a firm and secure grip for the object. For example, in one specific embodiment for an airfoil component, if a first finger assembly is equipped with padding to secure an airfoil fir tree section, a second finger assembly receives padding conformal to accommodate the airfoil blade shape.

Figure 6:
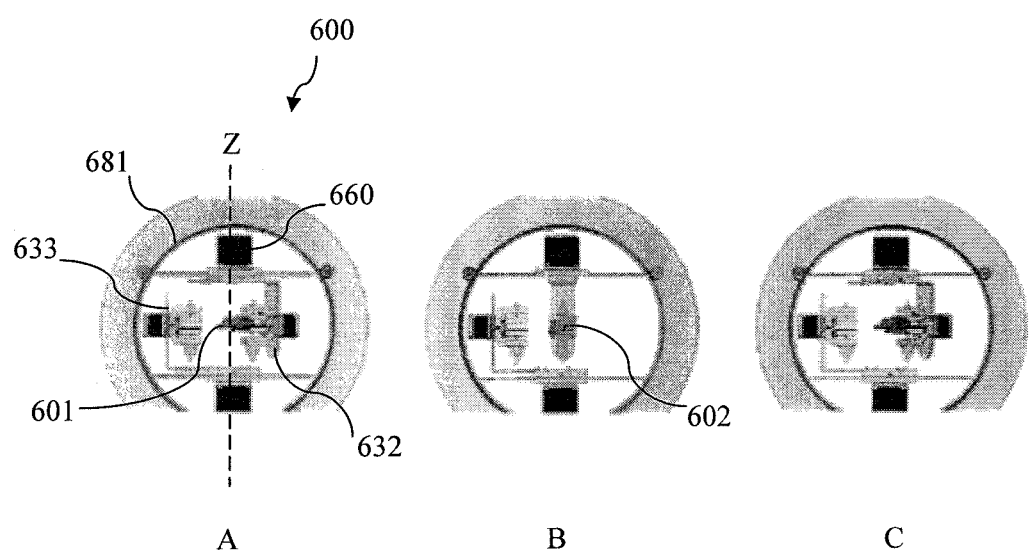
FIG. 6 is an illustration demonstrating movement of a portion of an embodiment of an object manipulation system.

FIG. 6 illustrates movement of a finger assembly 632 about a z-axis. The right-hand coordinate frame assumed for exemplary purpose includes an origin at a center of a circular frame 681 of an analysis system 600. The z-axis points upward and aligns with the axis of rotation of a motor drive system 660. This embodiment can provide substantially full angular rotation around the z-axis and finger assembly 632 can alter the position relative to another finger assembly 633. In one embodiment, the z-axis motion can facilitate analysis of relative bottom and top sections of an object as well as but not limited to components with intricate fillets, orifices, and labels (e.g., part number or serial number) engraved or embossed on a relative bottom surface of an object. In Position A of FIG. 6, finger assembly 632 is rotated partially around the z-axis by motor drive system 660 In Position B, finger assembly 632 is rotated around the z-axis by motor drive system 660 approximately 90° exposing a relative bottom surface 602 of object 601. In Position C, finger assembly 6 is returned to the original position.

Figure 7:
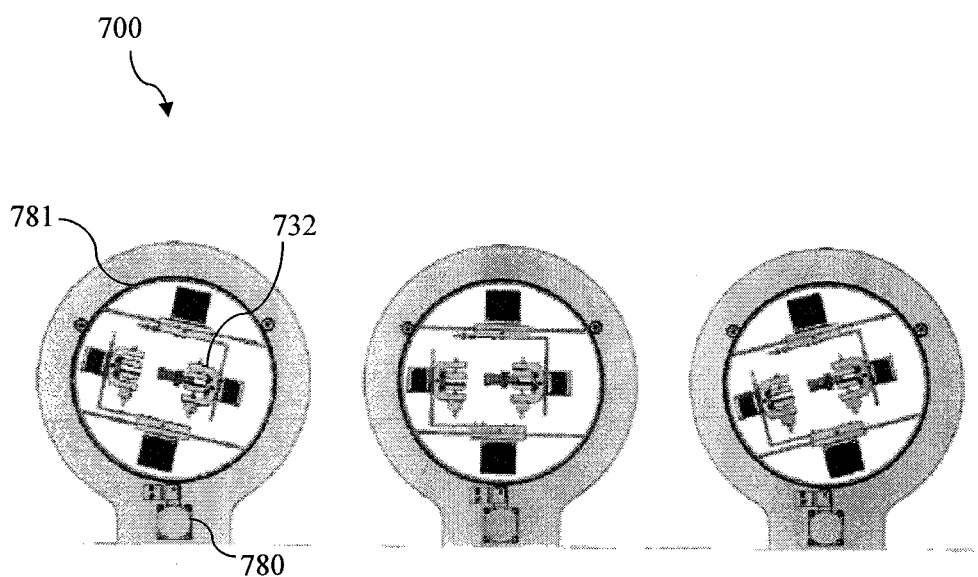
FIG. 7 is an illustration of one degree of freedom of an embodiment of an object manipulation system.

FIG. 7 illustrates movement of a finger assembly 732 about the x-axis. To achieve x-axis motion of finger assembly 732 in an automated object manipulation system 700, a rotary drive system 780 is employed. Rotary drive system 780 can be mounted below a circular frame 781. As shown, circular frame 781 is mechanically coupled to finger assembly 732 and rotary drive 780. In this particular embodiment, rotary drive system 780 causes circular frame 781 to rotate along a track. Circular frame 781 can be capable of rotating in related clockwise and counterclockwise directions. In some embodiments, circular frame 781 can be capable of rotating a substantially complete 360° during object manipulation. For a specific embodiment, a circular frame has on the circumferential wall a tooth-belt acting as a rack. The pinion on the rotary drive engages with the outer rack of the circular frame to facilitate the x-axis motion of a finger assembly.

Figure 8:
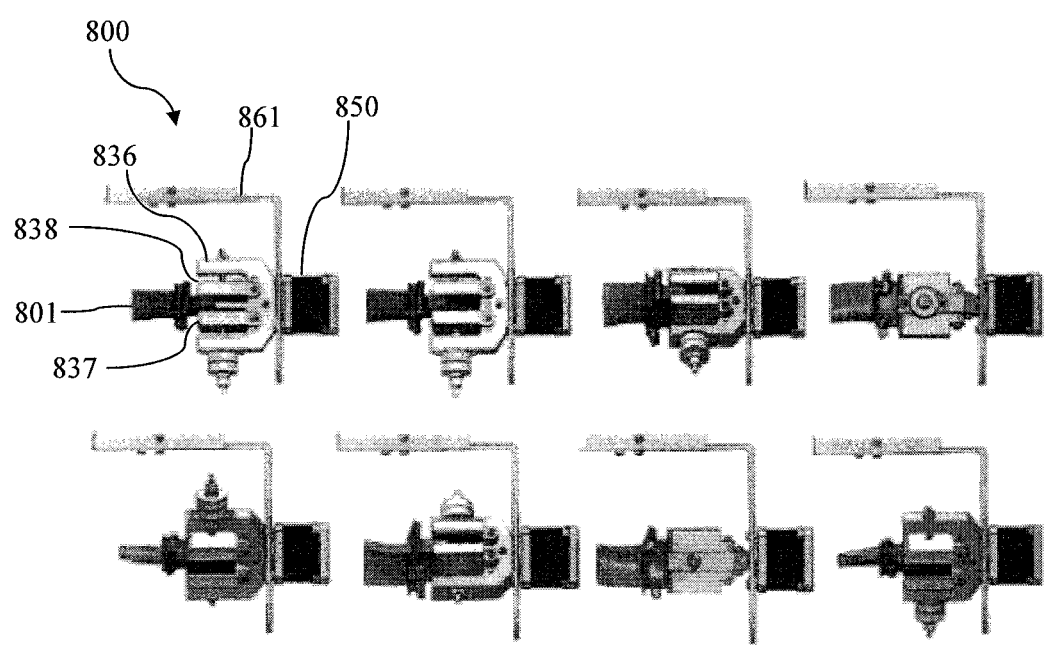
FIG. 8 is an illustration of another degree of freedom of an embodiment of an object manipulation system.

FIG. 8 illustrates movement of a finger assembly 800 about the y-axis. A y-axis motor drive 850 rotates a support bracket 836 holding an object 801 in a set of parallel jaws 837, 838. Substantially full 360-degree rotation of an object about the y-axis is achievable as a sequence of y-axis motions are shown in the series of illustrations in FIG. 8. A linking bracket 861 of finger assembly 800 can be adjustable. By adjusting the spacing of linking brackets 861 in one embodiment, finger assembly 800 can accommodate objects of differing dimensions.

In one embodiment, the x-axis can point towards a sensor system (not shown). In other embodiments, the sensor can be positioned to operate along another axis. The sensor system can include various equipment such as illumination and imaging devices. These devices can operate with the generation/detection of electromagnetic radiation, visible light, x-ray, ultraviolet and the like. A sensor can also be based on sound or physical detection. For another embodiment, the sensor can be located a fixed distance from the object manipulator along the symmetric axis of the circular frame. The sensor system can be applied for object assessment and/or analysis of an object presented by an object manipulation system.

An automated object manipulation system of the present application can include an automated analysis apparatus capable of improving the accuracy of repeated object manipulation with various components. In one embodiment, an automated object manipulation system can include a mechanical object manipulation support means having five degrees of freedom for supporting, aligning and positioning objects in proximity of an analysis tool. In another embodiment of the present application, an automated object manipulation system can adjust the location of an object to a position and orientation allowing analysis to be performed repeatedly and reliably.

One aspect of the present application is an apparatus including a support base; a finger assembly mechanically coupled to the support base; a first drive unit operable to rotate the finger assembly about a first axis; a second drive unit operable to rotate the finger assembly about a second axis; and a third drive unit operable to rotate the finger assembly about a third axis and further including a control system capable of positioning each of the first drive unit, second drive unit, and third drive unit.

Features of this aspect can include the finger assembly having a support bracket with a set of parallel jaws where the support bracket can be mechanically coupled to the first drive unit, an alignment mechanism structured to adjust the set of parallel jaws, a screw adjustment for the first finger and a linear actuator for the second finger, and a linking bracket mechanically coupled to the second drive unit. Another feature can include the set of parallel jaws having a first jaw with a first padded portion and a second jaw with a second padded portion. Yet another feature can include the support base having a circular frame mechanically coupled to the finger assembly and the third drive unit.

A further feature of this aspect can include a supplemental finger assembly with a supplemental first drive unit and a supplemental second drive unit; a supplemental support bracket having a set of supplemental parallel jaws where the supplemental support bracket is mechanically coupled to the supplemental first drive unit; a supplemental linking bracket mechanically coupled to the supplemental second drive unit; and a circular frame mechanically coupled to the finger assembly, the supplemental finger assembly and the third drive unit.

Another aspect of the present application is an apparatus including a mechanical support means structured to support an airfoil component; an object manipulation means structured to provide five degrees of freedom for supporting, aligning and positioning the airfoil component; and an automated control means.

Features of this aspect can include the automated control means being programmed for controlling, aligning, and positioning the airfoil component in relation to a sensor and where the automated control means can be structured to respond to a set of component data provided by a profiling assessment means and/or to continuously interpret a set of component data provided by an inspection assessment means and a profiling assessment means. Another feature of this aspect can include the profiling assessment means being structured to utilize at least one object surface feature to identify a manipulation program and utilize the manipulation program to identify and interpret a set of component data. Yet another feature can the object manipulation means being further structured to provide a finger assembly, a first drive unit operable to rotate the finger assembly about a first axis, a second drive unit operable to rotate the finger assembly about a second axis, and a third drive unit operable to rotate the finger assembly about a third axis and to provide a supplemental finger assembly, a supplemental first drive unit operable to rotate the supplemental finger assembly about a supplemental first axis, and a supplemental second drive unit operable to rotate the supplemental finger assembly about a supplemental second axis; and wherein the third drive unit is operable to rotate the supplemental finger assembly about the third axis.

Yet another aspect of the present application is a method including the steps of providing a component; operating a manipulation system having a finger assembly, a first drive unit operable to rotate the finger assembly about a first axis, a second drive unit operable to rotate the finger assembly about a second axis, a third drive unit operable to rotate the finger assembly about a third axis; conducting a profile assessment in response to the component; determining a manipulation program in response to the profile assessment; controlling the component with the manipulation system in response to the manipulation program; and presenting the component to a sensing system while controlling the component.

Still another aspect of the present application is an apparatus including an object manipulation system having a carrier that supports opposing first and second finger assemblies, each of the first and second finger assemblies capable of being rotated in unison together in the carrier about a carrier axis, the first finger assembly rotatable relative to the carrier about a first finger first axis and a first finger second axis, the first finger assembly also having a first finger mechanism to adjust a gap between a plurality of first fingers, the second finger assembly rotatable relative to the carrier about a second finger first axis and a second finger second axis, the second finger assembly also having a second finger mechanism to adjust a gap between a plurality of second fingers.

Features of this aspect can include wherein a spacing between the opposing first and second finger assemblies is configured to be adjusted through a support bracket; a first finger assembly drive unit structured to rotate the first finger assembly about the first finger first axis; wherein the first finger mechanism includes an actuator capable of altering a gap between the plurality of fingers; wherein the first finger mechanism includes an adjustment member capable of adjusting one of the plurality of fingers, the actuator capable of adjusting another of the plurality of fingers; wherein the first finger assembly is a mirror image of the second finger assembly; and wherein the carrier is rotatingly received in a static support structure.

Still a further aspect of the present application is a method that includes grasping a gas turbine engine component with a plurality of fingers of a first manipulator, handing off the gas turbine engine component to a second manipulator structured to rotate in a carriage that also includes the first manipulator, and rotating the gas turbine engine component about a first axis and a second axis fixed in the carriage prior to the handing off such that the first axis and second axis rotate with the carriage.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method comprising:
   grasping a gas turbine engine component with a plurality of fingers of a first manipulator;
   handing off the gas turbine engine component to a second manipulator structured to rotate in a carriage that also includes the first manipulator;
   rotating the gas turbine engine component about a first axis and a second axis fixed in the carriage prior to the handing off such that the first axis and second axis rotate with the carriage.

2. The method of claim 1, wherein the carriage comprises a circular frame, and wherein the circular frame is housed inside a cavity of a support structure.

3. The method of claim 1, further comprising adjusting a support bracket to adjust a spacing between the opposing first and second finger assemblies.

4. The method of claim 1, further comprising altering a gap between the plurality of fingers using an actuator.

5. The method of claim 1, wherein the first manipulator is a mirror image of the second manipulator.

6. The method of claim 2, wherein the first manipulator comprises:
   a first finger assembly comprising the plurality of fingers;
   a first drive unit operable to rotate the first finger assembly about a first axis;
   a second drive unit operable to rotate the first finger assembly about a second axis, wherein the second axis is substantially orthogonal to the first axis; and
   a third drive unit operable to rotate the first finger assembly about a third axis by rotating the circular frame about the third axis, wherein the third axis is substantially orthogonal to the first axis and substantially orthogonal to the second axis.

7. The method of claim 6, wherein the first manipulator comprises:
   a second finger assembly comprising a second plurality of fingers;
   a fourth drive unit operable to rotate the second finger assembly about a fourth axis;
   a fifth drive unit operable to rotate the second finger assembly about a fifth axis, wherein the fifth axis is substantially orthogonal to the fourth axis; and
   a sixth drive unit operable to rotate the finger assembly about the third axis by rotating the circular frame about the third axis, wherein the third axis is substantially orthogonal to the fourth axis and substantially orthogonal to the fifth axis.

* * * * *